(12) United States Patent
Fjord et al.

(10) Patent No.: US 10,595,990 B2
(45) Date of Patent: Mar. 24, 2020

(54) OSSEOINTEGRATIVE ADJUSTABLE OSSICULAR PROSTHESIS

(71) Applicant: Gyrus ACMI, Inc., Southborough, MA (US)

(72) Inventors: Thomas Fjord, Cordova, TN (US); Paul E. Yarbrough, Stanton, TN (US); Kevin C. Edwards, Olive Branch, MS (US)

(73) Assignee: Gyrus ACMI, Inc., Southborough, MA (US)

( * ) Notice: Subject to any disclaimer, the term of this patent is extended or adjusted under 35 U.S.C. 154(b) by 18 days.

(21) Appl. No.: 15/689,807

(22) Filed: Aug. 29, 2017

(65) Prior Publication Data
US 2018/0064531 A1    Mar. 8, 2018

Related U.S. Application Data

(60) Provisional application No. 62/383,678, filed on Sep. 6, 2016.

(51) Int. Cl.
*A61F 2/18* (2006.01)
*A61F 2/30* (2006.01)
*A61F 2/46* (2006.01)

(52) U.S. Cl.
CPC ............ *A61F 2/18* (2013.01); *A61F 2/30749* (2013.01); *A61F 2002/183* (2013.01);
(Continued)

(58) Field of Classification Search
CPC ................ A61F 2/18; A61F 2002/3038; A61F 2002/183; F16B 2/04; F16B 7/02;
(Continued)

(56) References Cited

U.S. PATENT DOCUMENTS 2,985,469 A * 5/1961 Bowman, Jr. ............ F16L 37/04
                                                            285/260
4,281,419 A   8/1981 Treace
(Continued)

FOREIGN PATENT DOCUMENTS

DE   202007012217 U1 * 11/2007 ............... A61F 2/18
WO   2016018160 A1    2/2016
WO   2016028171 A1    2/2016

OTHER PUBLICATIONS

Translation of DE 202007012217.*

*Primary Examiner* — Thomas Sweet
*Assistant Examiner* — Rebecca Lynee Zimmerman
(74) *Attorney, Agent, or Firm* — Harrington & Smith (57) ABSTRACT

An otologic prosthesis is disclosed. In accordance with some embodiments, the device includes a set of crimping prongs comprising a lattice structure provided on a surface of each crimping prong in the set of crimping prongs to support and promote osseointegration. In accordance with some embodiments, the stem and the TM plate are separate pieces configured to be attached by a snap-fit mechanism. In accordance with some embodiments, the device is an adjustable length prosthesis with an internalized sizing mechanism. In accordance with some embodiments, the device is adjustable by a rotatable joint that facilitates rotation of a first stem section with respect to a second stem section for adjustment and readjustment on a patient-specific basis.

16 Claims, 5 Drawing Sheets

(52) U.S. Cl.
CPC .............. *A61F 2002/3038* (2013.01); *A61F 2002/30299* (2013.01); *A61F 2002/30322* (2013.01); *A61F 2002/30604* (2013.01); *A61F 2002/30787* (2013.01); *A61F 2002/30985* (2013.01); *A61F 2002/4658* (2013.01); *A61F 2220/0008* (2013.01); *A61F 2220/0033* (2013.01); *A61F 2230/0093* (2013.01); *A61F 2240/001* (2013.01); *A61F 2250/006* (2013.01); *A61F 2250/0006* (2013.01); *A61F 2250/0007* (2013.01); *A61F 2250/0024* (2013.01); *A61F 2250/0052* (2013.01)

(58) Field of Classification Search
CPC .......... F16B 7/025; F16K 5/202; F16K 41/14; B65D 63/00; F16L 3/08
See application file for complete search history.

(56) References Cited

U.S. PATENT DOCUMENTS

| | | | |
|---|---|---|---|
| 4,317,471 A * | 3/1982 | King, Sr. | ................ F16L 37/05 137/115.16 |
| 6,168,625 B1 | 1/2001 | Prescott | |
| 6,432,139 B1 * | 8/2002 | Elies | ........................ A61F 2/18 623/10 |
| 7,815,826 B2 | 10/2010 | Serdy et al. | |
| 8,124,192 B2 | 2/2012 | Paasche et al. | |
| 8,192,489 B2 | 6/2012 | Edwards | |
| 8,920,496 B2 | 12/2014 | Abel et al. | |
| 9,216,081 B2 | 12/2015 | Steinhardt et al. | |
| 2003/0097178 A1 | 5/2003 | Roberson et al. | |
| 2004/0043051 A1 * | 3/2004 | Pilliar | .................... A61L 15/24 424/423 |
| 2007/0083263 A1 | 4/2007 | Steinhardt et al. | |
| 2008/0195201 A1 * | 8/2008 | Steinhardt | ................ A61F 2/18 623/10 |
| 2010/0010629 A1 | 1/2010 | Bhansali | |
| 2011/0054607 A1 | 3/2011 | Reitan et al. | |
| 2011/0076762 A1 | 3/2011 | Serdy et al. | |
| 2012/0251980 A1 | 10/2012 | Bassett et al. | |
| 2014/0094910 A1 | 4/2014 | Steinhardt et al. | |
| 2014/0163445 A1 | 6/2014 | Pallari et al. | |
| 2014/0172111 A1 * | 6/2014 | Lang | ...................... A61F 2/389 623/20.32 |
| 2014/0356472 A1 | 12/2014 | Oberhofer et al. | |
| 2015/0045903 A1 | 2/2015 | Neal | |
| 2015/0130099 A1 | 5/2015 | Ziabka et al. | |

\* cited by examiner

OSSEOINTEGRATIVE ADJUSTABLE OSSICULAR PROSTHESIS

RELATED APPLICATIONS

This application claims benefit under 35 U.S.C. § 119(e) of U.S. Provisional application Ser. No. 62/383,678 filed Sep. 6, 2016, the disclosure of which is incorporated by reference herein in its entirety.

FIELD OF THE DISCLOSURE

The embodiments of the present disclosure relate generally to an otologic implant. More particularly, the embodiments of the present disclosure relate to an adjustable otologic implant provided with osseointegrative lattice features.

BACKGROUND

Ossicular prostheses are commonly placed in patients with ossicular destruction or disruption due to cholesteatoma, chronic otitis media, or congenital ossicular malformation. Osseointegration refers to a direct structural and functional connection between ordered, living bone and the surface of a load-carrying implant. Currently, an implant is considered as osseointegrated when there is no progressive relative movement between the implant and the bone with which it has direct contact.

Surgical insertion of an implant is commonly performed to replace one or both of the middle and innermost middle ear ossicles (i.e. incus and stapes, respectively) following surgical removal of these structures. A stapedectomy is a procedure for surgical removal of the stapes of the ear. It is known to use ossicular and stapes replacement prostheses to replace one or more of the ear ossicles. It is known to use a crimping attachment method to adhere to middle ear bones; however, this method can be inconsistent and lead to complications during recovery.

Methods of adjusting the length of ossicular implants include cutting an indexed rod that is pulled through a tympanic membrane plate, hereinafter referred to as TM plate, of the implant or cutting a flexible shaft attached to the TM plate. These methods are external adjustment methods and such methods require an increased surface area on the shaft of the implant. This extra surface area may potentially be snagged on tissue and lead to complications during implantation and recovery. Additionally, when shortened, the indexed length adjustment may leave material that must be removed from the end of the TM plate. The clipping of this section can leave a rough surface, which is undesirable for an implant that will be placed into tissue.

Current mechanisms for deformable prostheses are only capable of being manipulated to a deformed angle a single time, after which the angle cannot be readjusted. Additionally, it is known to provide prostheses which are provided with preset angles; however, providing present angles can be limiting as they are not infinitely adjustable on a patient-specific basis and, therefore, the closest angle must be chosen for a procedure even if that angle is not optimized on a patient-specific basis.

SUMMARY

It would be advantageous in view of the above discussion to provide systems and methods for an improved otologic implant which is capable of meeting the above-identified needs. Such an implant would provide for a more stable device and better surgical outcomes.

The present disclosure provides an improved otologic implant, which may be achievable through additive manufacturing, which includes latticed interstitial spaces, and which allows bone to integrate with the prosthesis. The addition of latticed interstitial spaces in the prongs may allow for bone to integrate within the prosthesis, and also may allow for a more successful recovery.

The lattice structure allows for osseointegration of the middle ear bones. While traditional osseointegration of bones is best performed in a trabecular structure of rods and planes, the small size of the ossicular implants described here warrants a change in traditional design. It is contemplated that the structure uses a round repeating lattice with holes between 80 and 100 microns in diameter. This may help to increase surface area to be available for osseointegration. It is contemplated that such a lattice structure would yield an increase in osseointegration as well as soft tissue vascularization. It is contemplated that the otologic implant may be manufactured using 3D printing. In some embodiments, the otologic prosthesis is equipped with an internalized sizing mechanism. In some embodiments, the otologic prosthesis includes an adjustable or rotatable head.

Accordingly, pursuant to one aspect of the present invention, there is contemplated an otologic prosthesis, comprising a set of crimping prongs positioned at a distal end of the otologic prosthesis, the set of crimping prongs being joined at a proximal end thereof and open at a distal end thereof; a lattice structure provided on a surface of each crimping prong in the set of crimping prongs; and, a stem connecting the set of crimping prongs to a TM plate at a proximal end, wherein the stem and the TM plate are separate pieces configured to be attached by a snap-fit mechanism.

The invention may be further characterized by one or any combination of the features described herein, such as the lattice structure defines holes with a diameter of between 0.07 mm and 0.09 mm, the lattice structure defines holes with a diameter of between 0.09 mm and 0.11 mm, the snap-fit mechanism is an internalized sizing mechanism, the stem and the TM plate are configured to be removably attached, the stem comprises a female hub and the TM plate comprises a male plug, the TM plate comprises a female hub and the stem comprises a male plug, the otologic prosthesis is an adjustable length prosthesis, the otologic implant is manufactured using 3D printing.

Pursuant to another aspect of the present invention, there is contemplated an otologic prosthesis, comprising a set of crimping prongs positioned at a distal end, the set of crimping prongs being joined at a proximal end thereof and open at a distal end thereof, a lattice structure provided on a surface of each crimping prong in the set of crimping prongs, a stem connecting the set of crimping prongs to a TM plate at a proximal end, the stem comprising a first stem section and a second stem section, a rotatable head positioned between the first stem section and the second stem section, wherein the lattice structure promotes osseointegration.

The invention may be further characterized by one or any combination of the features described herein, such as a friction fit at the rotatable head, adjustment of the rotatable head is repeatable, the first stem section can rotate at an angle α from a plane parallel to the axis of the second stem section.

Pursuant to another aspect of the present invention, there is contemplated a method for sizing an otologic prosthesis, comprising placing a stem of an otologic prosthesis in the anatomy of a patient, measuring an appropriate stem length, cutting the stem, inserting a plug into a hub to secure the stem to a TM plate, and, forming the otologic prosthesis sized on a patient-specific basis.

The invention may be further characterized by one or any combination of the features described herein, such as the plug is connected to the TM plate and the hub is contained within the stem.

The claimed subject matter is not intended to be limited to a composition or method that must satisfy one or more of any stated objects or features of the devices described herein. It is also important to note that the claimed subject matter is not limited to the exemplary or primary embodiments described herein. Modifications and substitutions by one of ordinary skill in the art are considered to be within the scope of the disclosure.

Further aspects, advantages and areas of applicability will become apparent from the description provided herein. It should be understood that the description and specific examples are intended for purposes of illustration only and are not intended to limit the scope of the present disclosure.

These and other features of the present embodiments will be understood better by reading the following detailed description, taken together with the figures herein described. The accompanying drawings are not intended to be drawn to scale. For purposes of clarity, not every component may be labeled in every drawing.

DETAILED DESCRIPTION

The otologic prosthesis and associated methods described herein provide an otologic prosthesis with improved methods and structure for crimping attachment. Latticed interstitial spaces in the prongs of the crimping attachment structure can allow for bone to integrate within the prosthesis. Advantages may include a method of attachment which encourages osseointegration, yields a more stable connection to the region of interest, and yields a more successful recovery. In many embodiments, an internalized length adjustment method is used to adjust the implant's length to eliminate potential snagging of a patient's tissue during placement. In some embodiments, the internalized length adjustment method comprises use of frustoconical chambers configured about an internal circumference of the stem. The improved otologic prosthesis may also have the ability to manipulate the TM plate angle without compromising the structural integrity of the implant. In some cases, the otologic implant allows multiple manipulations until the desired angle between the TM plate and the stem is achieved. In some cases, the otologic implant allows multiple manipulations until the desired angle between the crimping prongs and the stem is achieved. In some cases, the otologic implant allows multiple manipulations until the desired angle between the crimping prongs and the TM plate is achieved.

The otologic prosthesis may also be referred to as an otologic implant, ossicular prosthesis or ossicular implant. The otologic implant may be a Partial Ossicular Replacement Prosthesis (PORP) or a Total Ossicular Replacement Prosthesis (TORP). In a TORP, TM plate would additionally connect to the footplate of the stapes. In a TORP, it may be desirable to manipulate the crimping prongs with respect to the stem, the TM plate with respect to the stem, the crimping prongs with respect to the TM plate, or some combination thereof.

The otologic prosthesis may be capable of providing a mechanism for improved osseointegration through the use of a lattice structure contained on the surface of crimping prongs. The otologic prosthesis may be capable of providing an internalized length adjustment mechanism for providing adjustment in length for a single prosthesis on a patient specific basis through a mechanism that protects the surrounding tissue of a patient following insertion by eliminating any externally located sharp edges. In some embodiments, the internalized length adjustment mechanism comprises frustoconical chambers configured about an internal circumference of the stem. The otologic prosthesis may be capable of providing rotational or angular adjustment through the use of a rotatable ball or pin joint connecting a first stem portion and a second stem portion. Such rotational adjustment may be readjustable, repeatable, and allow for manipulation of the TM plate angle without compromising the structural integrity of the implant.

Stem

A stem, as used herein, is configured to provide support between a set of crimping prongs located at a head or distal end and a TM plate located at a foot or proximal end of the otologic prosthesis of the present invention.

Structurally, in some embodiments, the stem comprises a single straight component connecting a head portion to a foot portion of the otologic implant. In some embodiments, the stem comprises a single straight component connecting a distal end portion to a proximal end portion of the otologic implant. In other embodiments, the stem comprises a first stem portion and a second stem portion. In some embodiments, the stem may include a slit formed along a proximal portion of the stem. In some embodiments, the stem may house an internalized sizing mechanism comprising a female snap-fit hub capable of receiving a male plug extending from a TM plate. In some embodiments, the internalized sizing mechanism comprises frustoconical chambers configured about an internal circumference of the stem. The female hub may be an indexed female hub capable of fixedly receiving a male plug following cutting the stem to the appropriate patient-specific size. The female hub may be provided with a series of sections that are formed with wider regions proximally and narrower regions distally, each section being connected by a tube portion with a diameter smaller than the wider regions, to provide a snap-fit for a male plug. A cylinder formed on the TM plate may surround the stem upon insertion of the male plug into the female hub.

In some embodiments, the stem may be capable of receiving a male plug fixedly or the stem may be removably insertable into a channel within the stem.

Functionally, the stem may provide an internalized length adjustment mechanism. The stem may provide a method to adjust the implant's length to eliminate potential snagging of a patient's tissue during placement. The stem may provide a snap-fit connection internally, externally, or both, to connect the TM plate, the head, or both. The slit of the stem may functionally allow for minor expansion of the proximal end of the stem during insertion of a male plug from the TM plate into the indexed female hub.

Crimping Prongs

Crimping prongs, as used herein, refer to a set of members located at a distal or head end of the otologic implant of the present invention. It is contemplated that the set of crimping prongs may include between two and six crimping prongs, preferably between three and five crimping prongs, most preferably four crimping prongs.

Structurally, the crimping prongs may be joined at a proximal end thereof and open at a distal end thereof. The crimping prongs may be formed integrally with the stem. The crimping prongs may be formed integrally with a first stem portion, a second stem portion, or both. The crimping prongs may be generally circular, generally rectangular, generally triangular, generally ovular, generally square, or the like. The crimping prongs may extend radially outward from a central axis formed by the stem. The crimping prongs may be curved proximally and straight distally. The crimping prongs may be straight proximally and curved distally. The crimping prongs may include a set of holes forming a lattice structure.

Functionally, the crimping prongs act to provide a surface to which bone from the inner ear will grow onto. As bone grows over the crimping prongs, the crimping prongs serve as a rigid structure anchoring the otologic prosthesis in position. Functionally, it is desirable to provide an improved surface architecture for promoting bone growth as well as bone ingrowth to ensure that the otologic prosthesis remains in position without further surgical intervention being required.

Improved Osseointegration

Improved osseointegration, as described herein, is achievable through the use of a lattice structure located on a surface of each crimping prong in a set of crimping prongs located at the head or distal end of the otologic prosthesis.

Structurally, a lattice structure may be provided on the surface of crimping prongs at the head of the otologic prosthesis. Latticed interstitial spaces may be provided in the prongs of the crimping attachment means to allow for bone to integrate within the prosthesis. The lattice may include a round repeating pattern with holes located in the surface structure of the crimping prongs. The lattice structure may comprise a set of holes, with each individual hole being between 60 and 120 microns in diameter, preferably between 70 and 110 microns in diameter, and most preferably between 80 and 100 microns in diameter. It is contemplated that the holes may be circular, square, triangular, or any other shape that would reasonable permit bone to grow therethrough and promote osseointegration. It is contemplated that the holes may further comprise growth factors, cells, active pharmaceutical agents, or the like, that may promote osseointegration.

Functionally, the latticed structure may encourage osseointegration, yield a more stable connection to the region of interest, and yield a more successful recovery. It is contemplated that use of growth factors, cells, active pharmaceutical agents, or the like may improve, speed up, or result in a stronger bond as the biological processes of osseointegration progress.

TM Plate

The TM plate, as described herein, provides end piece at the proximal, or foot, end of the otologic implant of the present invention. The TM plate generally provides support for tissue of the middle ear.

Structurally, the TM plate may consist of an outer annulus connected to an inner annulus via spokes. A cylinder may extend from the inner annulus toward the distal end of the otologic prosthesis. In some embodiments, a male plug may extend from a rod in the geometric center of the TM plate. Alternatively, the TM plate may include a female hub for receiving a male plug from a stem. The TM plate may be generally rounded, circular, or non-circular. The axis of the stem extending from the TM plate toward the crimping prongs can be centered on the TM plate or offset by some distance (i.e. the stem may be located centrally or offset from center on the TM plate). It is contemplated that, in the case where the stem is positioned offset from center on the TM plate, a second degree of motion and manipulation can be achieved where the two prosthesis portions can be rotated about the axis with respect to one another. This flexibility may be desirable for patients with complicated anatomy.

Functionally, the TM plate provides support for tissue of the middle ear and helps to maintain the otologic implant in position following insertion. Functionally, the TM plate of the present invention provides a covering to protect a proximal surface of the stem which may be cut to accommodate length adjustment on a patient-specific basis.

Internalized Length Adjustment

The internalized length adjustment method, as described herein, uses a two piece design, the two pieces being the TM plate and the stem. The TM plate and the stem may be attached using an annular snap-fit. In one configuration, the TM plate may include a male plug, while the stem may include an indexed female hub. In some embodiments, the indexed female hub comprises frustoconical chambers configured about an internal circumference of the stem. In an alternate configuration, the stem may include a male plug, while the TM plate may include an indexed female hub. The internalized length adjustment mechanism provides advantages over previous methods in that a rough surface on the outside of the implant is eliminated, thus eliminating the potential for tissue snagging.

Structurally, the internalized length adjustment mechanism is achieved by having separable TM plate and stem portions. This allows for a surgeon/user to intraoperatively size the implant, cut the stem accordingly, and subsequently snap the cut portion of the stem into the TM plate.

Functionally, the internalized length adjustment mechanism may improve patient outcomes via elimination of any externalized rough surfaces that might result from cutting the stem length to size. The internalized length adjustment mechanism may help to reduce the number of implants that hospitals would need to stock. A one-adjustable-size-fits-all otologic implant may be a preferable cost savings solution for users.

Rotatable Joint

The rotatable joint, as described herein, allows for adjustment and readjustment of the angle of a first stem portion with respect to a second stem portion, thereby changing the angle between crimping prongs located toward the implant head and the TM plate located at the implant foot.

Structurally, the rotatable joint may be a ball joint or a pin joint. This joint allows for rotation and manipulation of the angle of the stem with respect to the TM plate. The angle can be manipulated multiple times without affecting the integrity of the implant. The joint may be provided with a slight interference fit to allow friction to hold the final angled position in place. It is contemplated that the location of the rotatable joint with respect to the TM plate may vary. The rotatable joint may be closer to the crimping prongs at the head of the device or closer to the TM plate for different applications. For most procedures, the ball joint may be located relatively close to the TM plate. The position of the rotatable joint determines the length of first stem portion and the length of second stem portion. First stem portion may connect to second stem portion via rotatable joint. The rotatable joint may be a ball joint, a pin joint, or the like. Rotatable joint may be fixedly attached to the second stem portion, to the first stem portion, to the TM plate, to the crimping prongs, or to a combination thereof. Rotatable joint may be removably attached to the second stem portion, to the first stem portion, to the TM plate, to the crimping prongs, or to a combination thereof. The upper portion may be rotated at an angle α from a plane parallel to the axis of the lower portion. The angle α may not exceed more than a maximum of 90°, preferably the angle α may be in the range of 0-40°, most preferably the angle α may be in the range of 20-30°. It should be noted that not all anatomy would require angular adjustment. The upper portion may rotate in any plane from the plane parallel to the axis of the lower portion. Distance β is the distance between a center point of rotatable joint and the TM plate.

Functionally, the rotatable joint allows for manipulation of the TM plate angle without compromising the structural integrity of the implant. Functionally, the rotatable joint allows for multiple manipulations until the desired angle between the TM plate and the stem is achieved on a patient-specific basis. Rotatable joint allows otologic prosthesis of the present invention to switch between a straight configuration and a rotated configuration. The rotational movement achievable with the device of the present invention between the upper portion of the stem and the lower portion of the stem may be both reversible and readjustable.

Manufacturing Methods

It is contemplated that the otologic prosthesis described in the present invention may be manufactured by different techniques. For example, the otologic prosthesis may be manufactured through additive manufacturing techniques, or 3D printing. The otologic prosthesis may be manufactured via 3D printing in a single step in order to reduce stress at the rotatable socket joint by forming it in an integral fashion.

3D printing methods are described, for example, in U.S. Patent Application Publication No. 2011/0076762, U.S. Pat. No. 8,124,192, and U.S. Patent Application Publication No. 2014/0356472, which are incorporated by reference herein for all purposes. The process of 3D printing may involve, for example, depositing a layer of powder, depositing an aqueous binder liquid in selected places, allowing the aqueous binder liquid to dry, removing unbound powder, exposing the product to a vapor of an organic solvent, removing the organic solvent vapor, and optionally dissolving out water soluble particles to form a desired layer and/or a desired product formed by 3D printing. The process of 3D printing may involve selective sintering, use of electric field strength to transport power particles to an application surface, solidifying layers of a power material at the respective portions corresponding to the cross-section of an object, use of a shaking device to shake one or more powder containers, use of a stirring device to mix the contents of one or more power containers, use of a rotating or positioning device, and/or use of a solidification device which may include laser, heat radiation, use of electromagnetic radiation, or the like.

Additionally, the otologic prosthesis may be manufactured using purpose build equipment.

Figure 1:
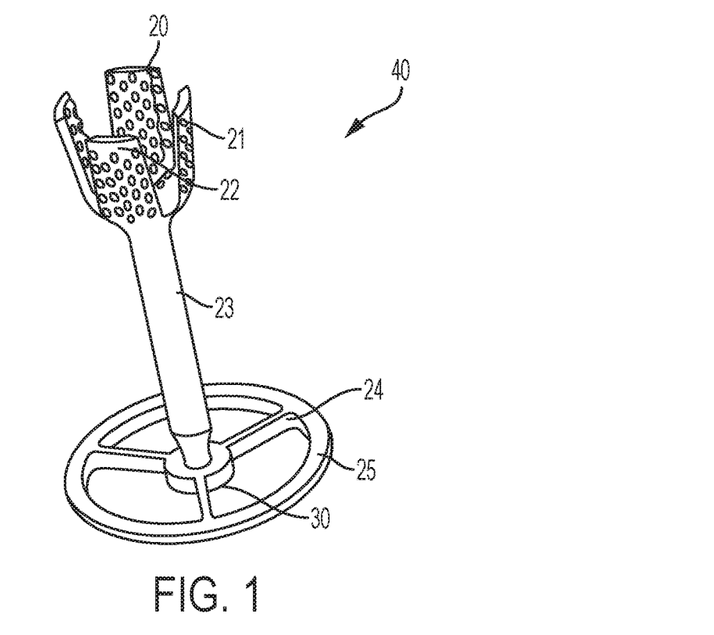
FIG. 1 illustrates a perspective view of one embodiment of an otologic prosthesis device.
Figure 2:
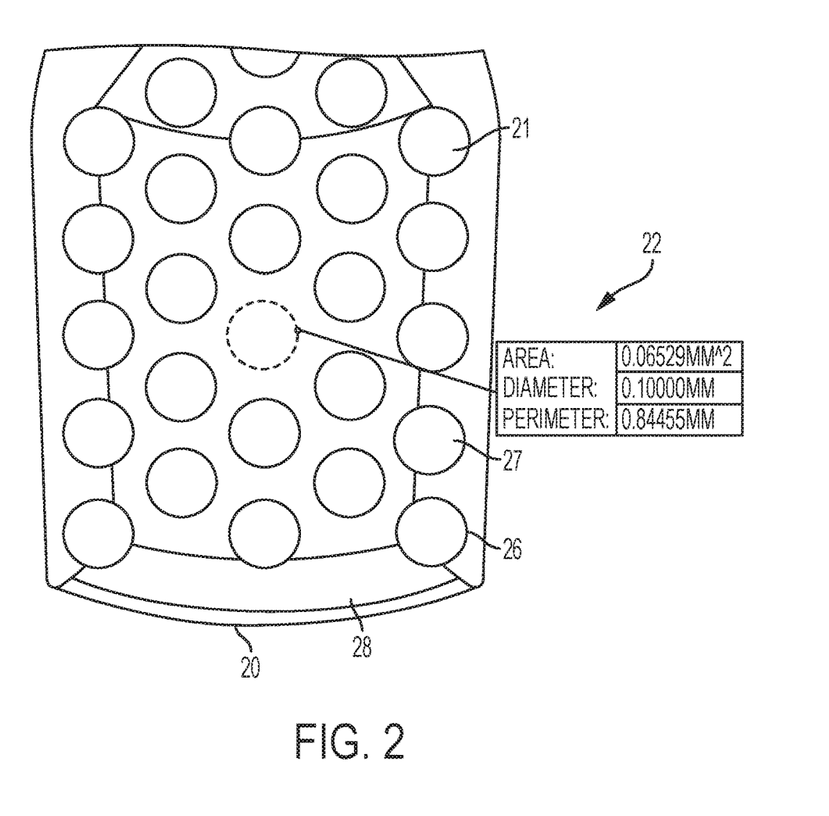
FIG. 2 illustrates a detailed view of one embodiment of the lattice structure of an otologic prosthesis device.

Turning now to the drawings to illustrate examples of embodiments of the present teachings, FIG. 1 details a perspective view of one embodiment of the device including a lattice structure 21 on the surface of a set of crimping prongs 22. A set of crimping prongs 22 is positioned toward a distal end 20 of the ossicular implant, the set of crimping prongs being joined at a proximal end thereof and extending radially outward at a distal end thereof. As illustrated four crimping prongs are provided and are each provided with a plurality of lattice openings 27 (see FIG. 2) in lattice structure 21. At a proximal end thereof, a TM plate 25 is provided. As illustrated (FIGS. 1, 3, 5-6), stem 23 is fixedly connected to a set of crimping prongs 22.

Figures 3, 4:
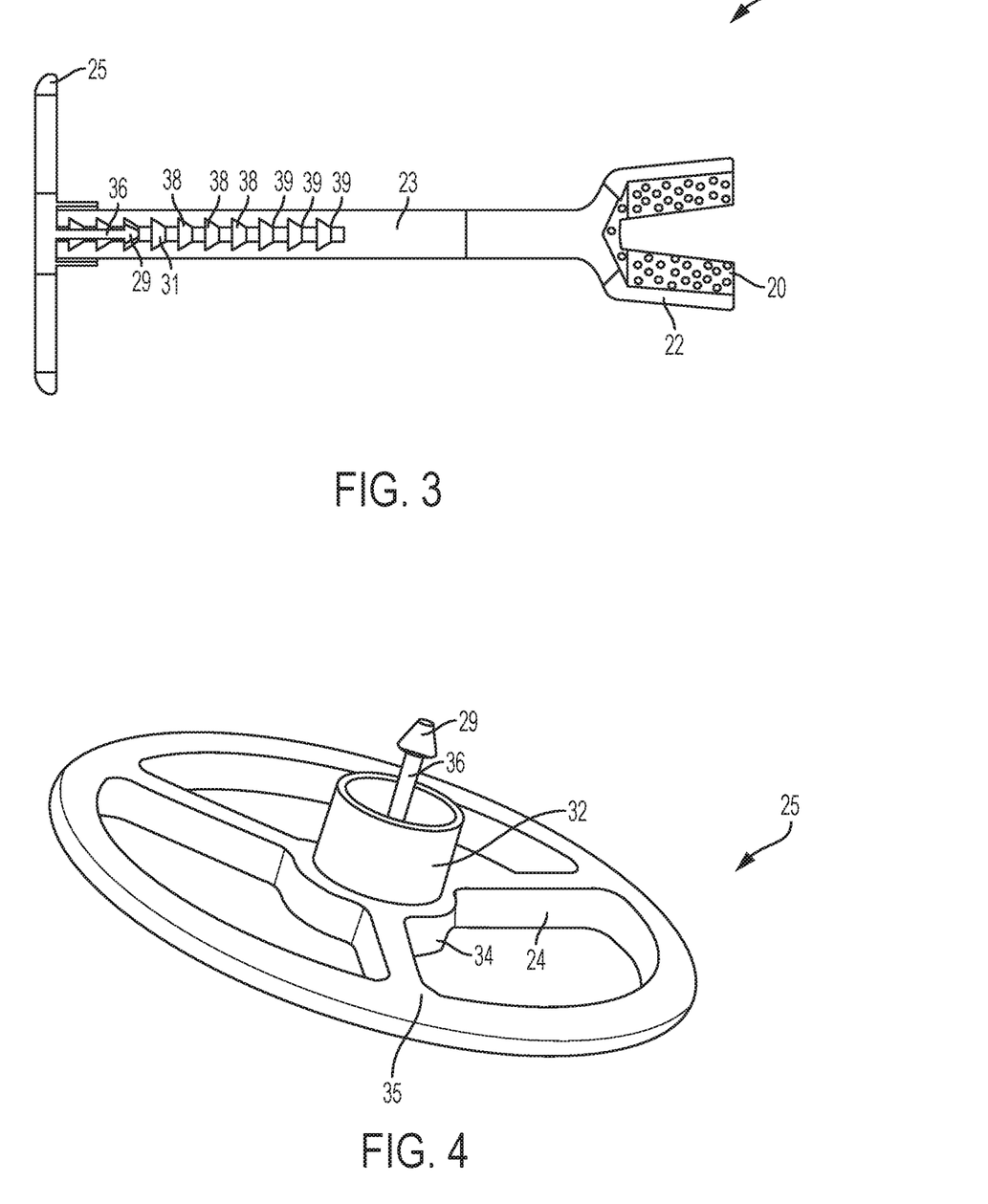
FIG. 3 illustrates a cross-sectional view of one embodiment of an otologic prosthesis device.
FIG. 4 illustrates a perspective view of an example TM plate of one embodiment of an otologic prosthesis device.

FIG. 4 illustrates a detailed view of TM plate 25, which consists of an outer annulus 35 connected to an inner annulus 34 via spokes 24. Cylinder 32 extends from inner annulus 34 toward the distal end 20 of otologic prosthesis 40. From the geometric center of the TM plate, male plug 29 extends from rod 36.

Male plug 29 is inserted into indexed female hub 31, as illustrated in FIG. 3. Indexed female hub provides a snap-fit internally to size the implant appropriately on a patient-specific basis and provides an improvement over existing technologies in that the patient-specific sizing is internalized, thus eliminating any potential sharp edges coming into contact with tissue of a patient following insertion of the otologic implant. FIG. 3 illustrates an example indexed female hub comprising frustoconical chambers configured about an internal circumference of the stem.

Figure 5:
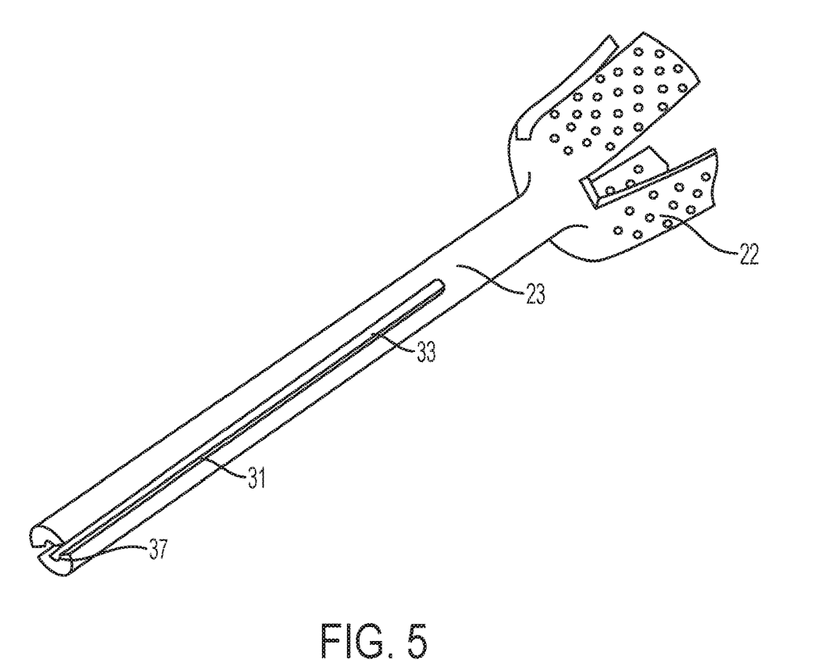
FIG. 5 illustrates a perspective view of a portion of an otologic prosthesis device.

Stem 23 may be trimmed at a proximal end 37 during the ossicular removal surgery (i.e. stapedectomy procedure) to be sized on a patient-specific basis. As shown in FIG. 5, slit 33 is provided to allow for minor expansion of the proximal end 37 of stem 23 during insertion of male plug 29 from TM plate 25 into indexed female hub 31. Female hub 31 is provided with a series of wider regions 38 proximally and narrower regions 39 distally to provide a snap-fit for male plug 29. As illustrated in FIG. 3, cylinder 32 surrounds stem 23 upon insertion of male plug 29 into female hub 31.

Figure 6:
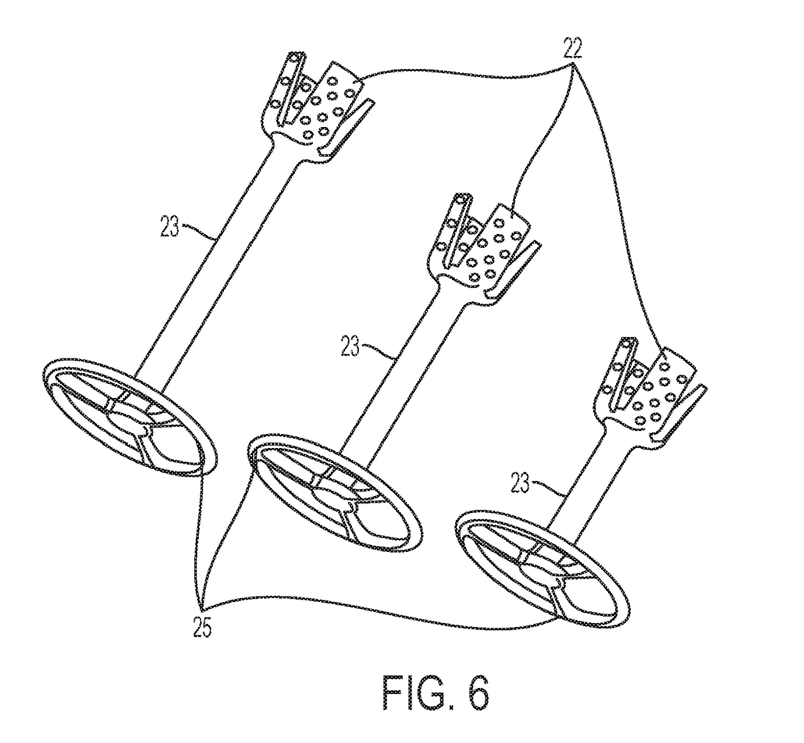
FIG. 6 illustrates a perspective view of different length implants of one embodiment of an otologic prosthesis device.

FIG. 6 illustrates three example lengths of otologic prosthesis 40. Different lengths may be achieved by cutting stem 23 following sizing during an ossicular removal surgery and subsequently inserting male plug 29, attached to TM plate 25, into female hub 31, contained within stem 23. The different otologic prosthesis lengths can be formed using the method of FIG. 9.

Figure 9:
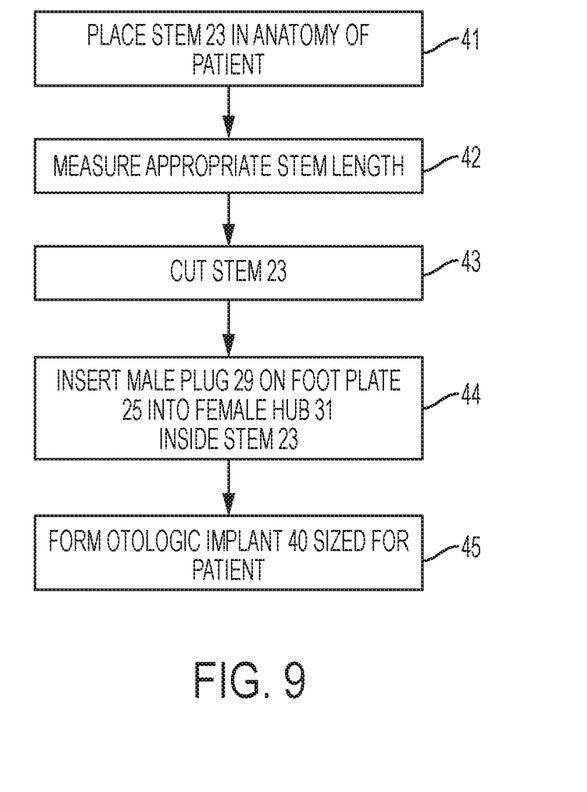
FIG. 9 illustrates a flow chart of one embodiment of a method for sizing and placing an otologic prosthesis device.

FIG. 9 details method steps for sizing otologic prosthesis 40. In step 41, stem 23 is placed in the anatomy of a patient. The anatomical region of interest for otologic implant 40 is inside the middle ear. In step 42, an appropriate length is measured for the stem in order to fit properly in the middle ear of the patient. In step 43, the stem is cut to the determined length. In step 44, male plug 29 on TM plate 25 is inserted into female hub 31 inside stem 23. In step 45, otologic implant 40 is formed and sized appropriately on a patient-specific basis.

Figure 7:
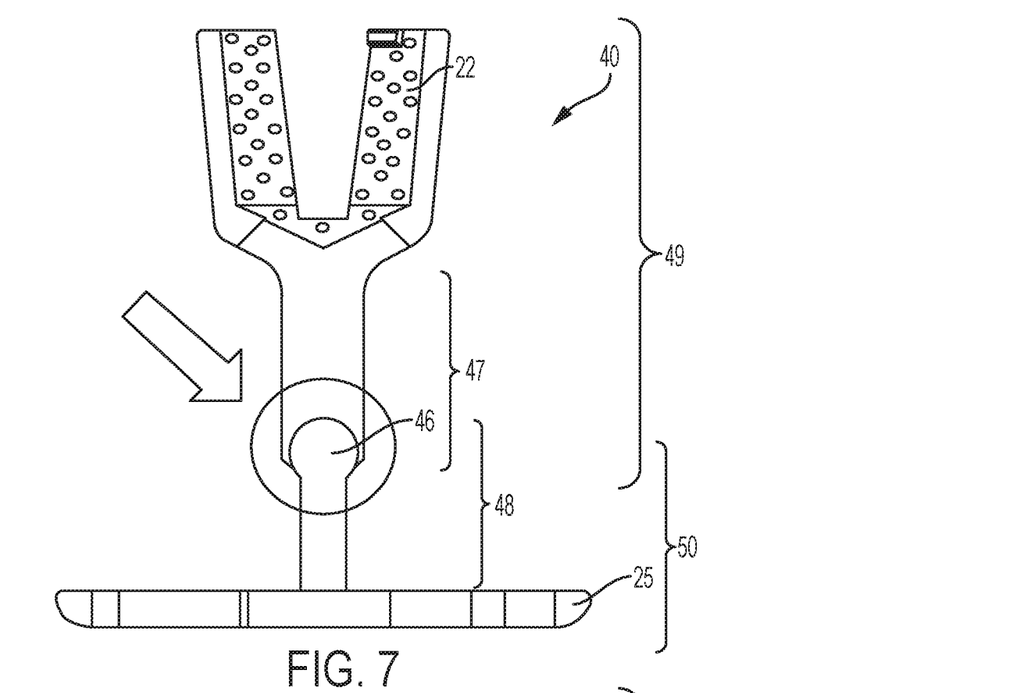
FIG. 7 illustrates a cross-sectional view of one embodiment of an otologic prosthesis device.

FIG. 7 illustrates otologic prosthesis 40 in a straight configuration. Rotatable joint 46 is illustrated at a point along the length of stem 23. The position of rotatable joint 46 determines the length of first stem portion 47 and the length of second stem portion 48. First stem portion 47 connects to second stem portion 48 via rotatable joint 46. As illustrated, rotatable joint 46 is a ball joint. As illustrated, rotatable joint 46 is fixedly attached to second stem portion 48.

Figure 8:
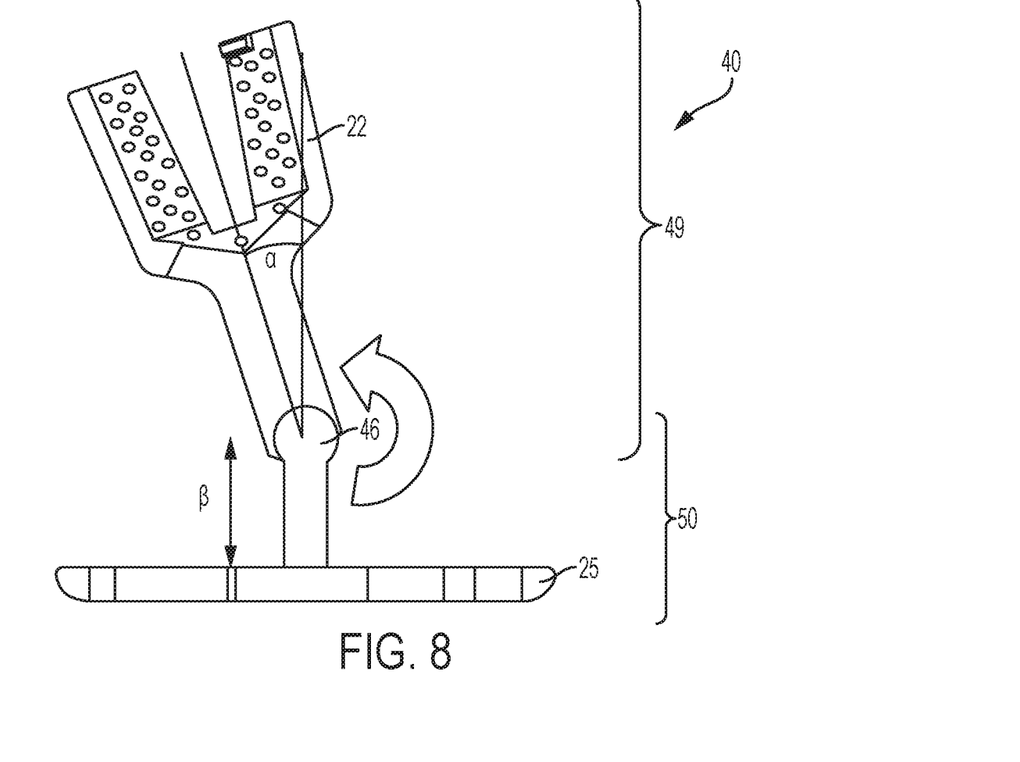
FIG. 8 illustrates a cross-sectional view of one embodiment of an otologic prosthesis device.

FIG. 8 illustrates otologic prosthesis 40 in a rotated position. Upper portion 49 is rotated at an angle α from a plane parallel to the axis of lower portion 50. Upper portion 49 may be rotated in any plane an angle α from a plane parallel to the axis of lower portion 50. Distance β is illustrated as the distance between a center point of rotatable joint and TM plate 25. The rotational movement achievable with the device of the present invention between upper portion 49 and lower portion 50 is both reversible and readjustable.

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated herein in their entirety herein by reference.

ELEMENT NUMBERS

20 Distal end of implant
21 Lattice
22 Crimping prong
23 Stem
24 Spoke
25 TM plate
26 Outer circumference of lattice
27 Lattice opening
28 Bevel
29 Male plug
30 Proximal end of implant
31 Indexed female hub
32 Cylinder
33 Slit
34 Inner annulus
35 Outer annulus
36 Rod
37 Stem proximal end
38 Wider region
39 Narrower region
40 Otologic prosthesis
41 Place stem 23 in anatomy of patient
42 Measure appropriate stem length
43 Cut stem
44 Insert male plug 29 on TM plate 25 into female hub 31 inside stem 23
45 Form otologic implant 40 sized for patient
46 Rotatable joint
47 First stem portion
48 Second stem portion
49 Upper portion
50 Lower portion
α Angle of rotation of head with respect to TM plate
β Distance between center point of rotatable joint and TM plate

What is claimed is:

1. An otologic prosthesis, comprising:
   a set of crimping prongs positioned at a distal end of the otologic prosthesis, the set of crimping prongs being joined at a proximal end thereof and open at a distal end thereof;
   a lattice structure provided on a surface of each crimping prong in the set of crimping prongs; and
   a stem connecting the set of crimping prongs to a TM plate at a proximal end, the stem comprising an annular snap-fit mechanism, the annular snap-fit mechanism comprising frustoconical chambers configured about an internal circumference of the stem, the TM plate comprising a male plug,
   wherein the male plug is configured to be inserted into the annular snap-fit mechanism to secure the stem to the TM plate,
   wherein the stem is configured to be cut for sizing.

2. The otologic prosthesis of claim 1, wherein the lattice structure defines holes with a diameter of between 0.07 mm and 0.09 mm.

3. The otologic prosthesis of claim 1, wherein the lattice structure defines holes with a diameter of between 0.09 mm and 0.11 mm.

4. The otologic prosthesis of claim 1, wherein the annular snap-fit mechanism is an internalized sizing mechanism.

5. The otologic prosthesis of claim 1, wherein the stem and the TM plate are configured to be removably attached.

6. The otologic prosthesis of claim 1, wherein the otologic prosthesis is an adjustable length prosthesis.

7. The otologic prosthesis of claim 1, wherein the otologic implant is manufactured using 3D printing.

8. The otologic prosthesis of claim 1, wherein the frustoconical chambers comprise a series of wider regions proximally and narrower regions distally.

9. The otologic prosthesis of claim 1, further comprising a slit formed on a proximal portion of the stem configured to provide for minor expansion of the proximal end.

10. The otologic prosthesis of claim 1, wherein each of the frustoconical chambers is separated by a cylindrical section formed in the internal circumference of the stem.

11. A method for sizing an otologic prosthesis, the method comprising:
    placing a stem of an otologic prosthesis in the anatomy of a patient, the stem comprising an annular snap-fit mechanism, the annular snap-fit mechanism comprising frustoconical chambers configured about an internal circumference of the stem;
    measuring an appropriate stem length;
    cutting the stem;
    inserting a frustoconical plug into the annular snap-fit mechanism to secure the stem to a TM plate; and
    forming the otologic prosthesis sized on a patient-specific basis.

12. The method of claim 11, wherein the plug is connected to the TM plate and the hub is contained within the stem.

13. The method of claim 11, wherein the frustoconical chambers comprise a series of wider regions proximally and narrower regions distally.

14. The method of claim 11, further comprising a slit formed on a proximal portion of the stem configured to provide for minor expansion of the proximal end.

15. An otologic prosthesis, comprising:
    a set of crimping prongs positioned at a distal end of the otologic prosthesis, the set of crimping prongs being joined at a proximal end thereof and open at a distal end thereof;
    a lattice structure provided on a surface of each crimping prong in the set of crimping prongs; and
    a stem connecting the set of crimping prongs to a TM plate at a proximal end, the stem comprising an annular snap-fit mechanism and a slit formed along a proximal portion of the stem, the TM plate comprising a plug,
    wherein the plug is configured to be inserted into the annular snap-fit mechanism to secure the stem to the TM plate,
    wherein the stem is configured to be cut for sizing.

16. The otologic prosthesis of claim 15, wherein the annular snap-fit mechanism comprises an indexed hub.

\* \* \* \* \*